United States Patent
Sano et al.

(10) Patent No.: US 10,080,502 B2
(45) Date of Patent: Sep. 25, 2018

(54) SOLENOID VALVE AND ELECTRONIC BLOOD PRESSURE MONITOR EQUIPPED WITH THE SAME

(71) Applicant: OMRON HEALTHCARE Co., Ltd., Kyoto (JP)

(72) Inventors: Yoshihiko Sano, Kyoto (JP); Gaku Hasegawa, Kyoto (JP); Hironori Sato, Kyoto (JP); Hiroyuki Kinoshita, Kyoto (JP); Toshihiko Ogura, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 371 days.

(21) Appl. No.: 14/991,647

(22) Filed: Jan. 8, 2016

(65) Prior Publication Data
US 2016/0120417 A1    May 5, 2016

Related U.S. Application Data

(63) Continuation of application No. PCT/JP2014/067002, filed on Jun. 26, 2014.

(30) Foreign Application Priority Data

Jul. 10, 2013 (JP) .................................. 2013-144390

(51) Int. Cl.
*A61B 5/02* (2006.01)
*A61B 5/0235* (2006.01)
*F16K 31/06* (2006.01)

(52) U.S. Cl.
CPC ............ *A61B 5/0235* (2013.01); *F16K 31/06* (2013.01); *F16K 31/0675* (2013.01)

(58) Field of Classification Search
CPC .. F16K 31/061; F16K 31/0606; A61B 5/0235
See application file for complete search history.

(56) References Cited

U.S. PATENT DOCUMENTS 3,185,177 A * 5/1965 Brandenberg ...... F16K 31/0606
137/625.27
5,522,424 A * 6/1996 Dalton, Jr. .......... F15B 13/0405
137/560

(Continued)

FOREIGN PATENT DOCUMENTS

JP          10238647 A    9/1998
JP         200170263 A    3/2001

(Continued)

OTHER PUBLICATIONS

International Search Report issued in corresponding International Application No. PCT/JP2014/067002, dated Sep. 2, 2014 (5 pages).

*Primary Examiner* — Michael R Bloch
(74) *Attorney, Agent, or Firm* — Osha Liang LLP

(57) ABSTRACT

In a solenoid valve, a bobbin and a solenoid coil are accommodated in a casing. A rod-shaped plunger is slidably inserted into the bobbin. A core provided with a flow port through which a fluid flows is disposed on one side of the casing. A valve body is attached to one end opposing the flow port of the plunger. In a non-operating period during which a solenoid coil is in a non-energized state, the valve body moves away from the flow port due to the biasing force applied by the biasing portion and another end of the plunger protrudes outward from the casing through the through hole, abuts against lock portions disposed outside of the casing, and is thereby locked. The lock portions can be elastically deformed by an external force such that separation of the plunger and the valve body from the casing is allowed.

7 Claims, 11 Drawing Sheets

(56) References Cited

U.S. PATENT DOCUMENTS

| | | | |
|---|---|---|---|
| 5,992,461 A | * | 11/1999 | Gilmore ................. H01F 7/081 137/625.65 |
| 2004/0024325 A1 | * | 2/2004 | Nishibayashi ......... A61B 5/022 600/492 |
| 2006/0006967 A1 | * | 1/2006 | Sano ................... A61B 5/0235 335/220 |
| 2007/0131887 A1 | | 6/2007 | Huang |

FOREIGN PATENT DOCUMENTS

| | | |
|---|---|---|
| JP | 2002276839 A | 9/2002 |
| JP | 3095598 U | 8/2003 |
| JP | 2006029394 A | 2/2006 |

\* cited by examiner

SOLENOID VALVE AND ELECTRONIC BLOOD PRESSURE MONITOR EQUIPPED WITH THE SAME

TECHNICAL FIELD

The present invention relates to solenoid valves, and more specifically relates to a solenoid valve that opens and closes due to a plunger (movable iron core) being moved with a magnetic force of a solenoid coil.

Also, the present invention relates to an electronic blood pressure monitor equipped with such a solenoid valve.

BACKGROUND ART

Conventionally, the solenoid valve disclosed in Patent Document 1 (JP 3095598U) for example is known as a solenoid valve of a type that can variably control the flow amount of a fluid. The solenoid valve includes a U-shaped yoke, and a fixed cover that is fixed by compression so as to close an open end of the yoke. A bobbin and a solenoid coil wound around the bobbin are housed therein. Furthermore, a rod-shaped plunger (movable iron core) is slidably inserted in the bobbin. A core (bottom rod) provided with a flow port through which the fluid flows is disposed on a wall surface of the yoke opposed to the fixed cover. A buffer material serving as the valve body is attached to one end of the plunger, and the buffer material opposes the flow port of the core. In a non-operating period during which the solenoid coil is in a non-energized state, the buffer material attached to the one end of the plunger is separated from the flow port due to a biasing force applied by a compressed spring. In an operating period during which the solenoid coil is in an energized state, the buffer material is moved along with the plunger inside of the bobbin against the biasing force applied by the compressed spring due to a magnetic force generated by the solenoid coil. Accordingly, the flow amount of the fluid flowing through the flow port is adjusted.

Another end on the side opposite to the one end of the plunger protrudes outward from the fixed cover through a through hole. Also, the other end is covered by an approximately U-shaped protruding cover that extends outward from the bobbin through the through hole.

CITATION LIST

Patent Literature

Patent Document 1: JP 3095598U

SUMMARY OF INVENTION

Incidentally, sometimes this kind of solenoid valve is required to have various different flow amount properties depending on its use. Also, if debris or the like becomes jammed between the flow port of the core and the valve body (buffer material) during use, the solenoid valve needs to be disassembled to perform maintenance.

However, with the solenoid valve according to Patent Document 1, since the yoke and the fixed cover are fixed by compression and the other end of the plunger is covered by the protruding cover (which is formed integrally with the bobbin), disassembly is difficult to perform, which makes it difficult to replace the plunger and the valve body. As a result, in order to realize various different flow amount properties, there has been no choice but to change the entire solenoid valve and increase the number of models thereof.

Also, if debris or the like is jammed between the flow port of the core and the valve body during use, internal maintenance is difficult to perform, and therefore there has been no choice but to replace the entire solenoid valve.

In view of this, one or more embodiments of the claimed invention aim to provide a solenoid valve whose plunger and valve body can be exchanged easily, according to which various different flow amount properties can be realized easily without changing the entire solenoid valve, and according to which internal maintenance is easy to perform.

Also, one or more embodiments of the claimed invention aim to provide an electronic blood pressure monitor equipped with such a solenoid valve.

Accordingly, a solenoid valve according to one or more embodiments of the claimed invention is a solenoid valve capable of variably controlling a flow amount of a fluid including a casing, a bobbin accommodated in the casing and a solenoid coil wound around the bobbin, a rod-shaped plunger slidably inserted in the bobbin, a core that is provided with a flow port through which a fluid flows and is disposed on a side of the casing opposing one end of the plunger, a valve body that is provided on the one end of the plunger and is disposed so as to oppose the flow port, and a biasing portion that biases the plunger in a direction of moving away from the core, wherein, in a non-operating period, during which the solenoid coil is in a non-energized state, the valve body provided on the one end of the plunger moves away from the flow port and another end opposite to the one end of the plunger protrudes outward from the casing through a through hole, abuts against a lock portion disposed outside of the casing, and is thereby locked, wherein in a working period during which the solenoid coil is in an energized state, the flow amount of the fluid flowing through the flow port is adjusted due to the plunger and the valve body being moved inside the bobbin against the biasing force applied by the biasing portion, due to a magnetic force generated by the solenoid coil, and wherein the lock portion can deform elastically due to an external force such that separation of the plunger and the valve body from the casing is allowed.

In the present specification, an "external force" means a force received from an external element that is not a constituent element of the solenoid valve.

The solenoid valve according to one or more embodiments of the claimed invention is used in the following mode. That is, in a non-operating period during which the solenoid coil is in a non-energized state, the valve body provided on the one end of the plunger is separated from the flow port by the biasing force applied by the biasing portion, and the other end opposite to the one end of the plunger protrudes outward from the casing through the through hole, abuts against the lock portion disposed outside of the casing, and is thereby locked (this state of the lock portion will be referred to as the "closed state"). In an operating period during which the solenoid coil is in an energized state, the flow amount of the fluid flowing through the flow port is adjusted due to the plunger and the valve body being moved inside the bobbin against the biasing force applied by the biasing portion due to a magnetic force generated by the solenoid coil.

If disassembly is needed in order to realize various different flow amount properties and the like, in the non-operating period during which the solenoid coil is in the non-energized state, the lock portion is elastically deformed by an external force so as to be put into a state in which the plunger can be passed therethrough (this will be referred to as the "open state"). The plunger and the valve body are separated from the casing (i.e., the bobbin) through the lock portion in the open state. In their place, a new plunger with a valve body provided at one end is inserted into the interior of the casing (or more accurately, the bobbin) through the lock portion in the open state and the through hole, in the direction in which the valve body opposes the flow port of the core. Thereafter, when the external force on the lock portion is removed, the lock portion returns to its original shape and enters the closed state, in which passage of the newly-inserted plunger is prohibited. That is, in the non-operating period, the other end of the newly-inserted plunger (the end portion on the side opposite to the one end on which the valve body is provided) protrudes outward from the casing through the through hole, abuts against the lock portion, and is thereby locked. Thus, with the solenoid valve, the plunger and the valve body can be replaced easily. Accordingly, various different flow rate properties can be easily realized without changing the entire solenoid valve. Also, internal maintenance can be easily performed.

Note that after the original plunger and valve body are separated from the casing, the external force on the lock portion may be temporarily removed, and immediately before inserting the new plunger and the valve body, the lock portion may be elastically deformed again by the external force so as to be brought into the open state.

With a solenoid valve according to an embodiment, the bobbin includes a main body portion accommodated in the casing, a first extended portion that is formed integrally with the main body portion and extends outward of the casing through the through hole, and the first extended portion constitutes the lock portion.

With the solenoid valve according to the embodiment, the lock portion is composed of the first extended portion of the bobbin, that is, a portion that is formed integrally with the main body portion and extends outward from the casing through the through hole. Accordingly, it is not necessary to bother to increase the number of components in order to provide the lock portion. As a result, it is possible to avoid a case in which the manufacturing cost of the solenoid valve rises.

With a solenoid valve according to an embodiment, the lock portion includes an arm portion that extends outward of the casing through the through hole along a movement path of the plunger, a leading end side of the arm portion being able to bend in a direction of moving away from the movement path of the plunger due to the external force, a hook portion that extends substantially orthogonally toward the movement path of the plunger from the leading end of the arm portion and has a cut-off leading end, and the hook portion locks the other end of the plunger during the non-operating period.

In the present specification, the "movement path" of the plunger means the path of movement in the longitudinal direction of the plunger and includes not only the path on which the plunger moves during operation, but also the path for when the plunger is separated from the casing.

With the solenoid valve according to the embodiment, the lock portion includes an arm portion and a hook portion. In the non-operating period, the other end of the plunger (the end portion that protrudes outward from the casing through a through hole) is locked by the hook portion. If the need for disassembly arises, the arm portion is bent in a direction of moving away from the movement path of the plunger, as the elastic deformation by the external force. Accompanying this, the hook portion moves away from the movement path of the plunger, whereby the lock portion enters the open state. Accordingly, the plunger and the valve body can be separated from the casing (i.e., the bobbin) through the lock portion in the open state. Also, the new plunger and valve body are inserted into the casing through the lock portion in the open state and the through hole, and thereafter, if the external force on the arm portion is removed, the arm portion and the hook portion return to their original shapes and positions, thereby entering the closed state. That is, in the non-operating period, the other end of the new plunger protrudes outward from the casing through the through hole, abuts against the hook portion, and is thereby locked.

Note that with the solenoid valve disclosed in Patent Document 1, the substantially U-shaped protruding cover extends outward from the bobbin body through the through hole in order to lock the plunger. The protruding cover and the bobbin body are formed integrally using a plastic material with a certain degree of mechanical strength (resistance to deformation). The bobbin body and the protruding cover are provided with a certain degree of mechanical strength in order to stabilize the shape of the solenoid coil wound around the bobbin body, stabilize the position of the solenoid coil with respect to the casing (yoke and fixed cover), and reliably lock the plunger using the protruding cover. For this reason, it is difficult to put the U-shaped protruding cover into the open state using elastic deformation.

With a solenoid valve according to an embodiment, the through hole includes a main region having a shape that substantially corresponds with a cross-section of the plunger, and an extended region that is continuous with the main region and is extended in order to allow the arm portion to pass therethrough, and a gap is provided between the arm portion and a face opposing the arm portion of the extended region, with respect to at least the direction in which the arm portion moves away from the movement path of the plunger.

With the solenoid valve according to the embodiment, a gap is provided between the arm portion and the face opposed to the aim portion of the extended region, in at least the direction in which the arm portion moves away from the movement path of the plunger. Accordingly, when the arm portion is bent in the direction of moving away from the movement path of the plunger as the elastic deformation by the external force, the arm portion bends easily from the base continuous with the main body portion of the bobbin while reducing the gap without coming into contact with the face opposing the arm portion of the extended region. Accordingly, the lock portion can be put into the open state using a smaller external force. As a result, it is possible to avoid a situation in which the arm portion breaks during deformation for putting the lock portion into the open state.

With a solenoid valve according to an embodiment, a tapered surface that is open toward the outside of the casing is provided on a side opposite to a side that abuts against the plunger of the hook portion.

It is assumed that the lock portion is in the closed state when the new plunger and valve body are to be inserted after the original plunger and valve body have been separated from the casing. Here, with the solenoid valve of the embodiment, a tapered surface that is open toward the outside of the casing is provided on a side opposite to a side that abuts against the plunger of the hook portion. Accordingly, when the new plunger is to be inserted into the interior from the outside of the casing along the movement path, first, the edge of the one end of the new plunger (the end portion on which the valve body is provided) abuts against the tapered surface of the hook portion. According to this, from the one end of the new plunger, the lock portion (the hook portion thereof) receives the force that bends the arm portion in the direction of moving away from the movement path of the plunger as the external force. Next, when the new plunger is pushed into the interior of the casing, the arm portion bends in the direction of moving away from the movement path of the plunger, the hook portion moves away from the movement path of the plunger, and the lock portion enters the open state. When the new plunger is pushed further into the interior of the casing, the hook portion comes into contact with the external circumferential face of the new plunger and enters a state of receiving, from the external circumferential face, a force that bends the arm portion in the direction of moving away from the movement path of the plunger. Accordingly, the lock portion maintains the open state. In view of this, while the open state is maintained, the new plunger and valve body are inserted into the easing through the lock portion in the open state and the through hole. Also, when the new plunger and valve body are completely inserted into the interior of the casing, the lock portion returns to its original shape and enters the closed state in which passage of the newly-inserted plunger is prohibited. If the new plunger and valve body are thus inserted, the lock portion receives an external force from the new plunger that is being pushed in, and thus enters the open state. Accordingly, there is no need to provide a separate external force to the lock portion, which is convenient.

With a solenoid valve according to an embodiment, the lock portion includes a plurality of sets that are each composed of the arm portion and the hook portion.

With the solenoid valve according to the embodiment, the lock portion includes a plurality of sets that are each composed of the arm portion and the hook portion. Accordingly, in a non-operating period, the strength of locking the other end of the plunger is increased. Also, even if one arm portion breaks at the time of deformation for putting the lock portion in the open state, in the non-operating period, the other end of the plunger can be locked with the arm portions and hook portions of the remaining sets.

With a solenoid valve according to an embodiment, the casing has a U-shaped yoke and a plate-shaped yoke lid that closes an open end of the yoke, and the through hole is formed in the yoke lid, the bobbin has a second extended portion and a third extended portion formed integrally with the main body portion, and the second extended portion and the third extended portion come into contact with a pair of opposing sides of the yoke lid and extend outward of the casing, parallel to the movement path of the plunger.

With the solenoid valve according to the embodiment, the bobbin has a second extended portion and a third extended portion that are formed integrally with the main body portion. The second extended portion and the third extended portion come into contact with a pair of opposing sides of the yoke lid and extend outward of the casing, parallel to the movement path of the plunger. That is, the second extended portion and the third extended portion of the bobbin sandwich the yoke lid in the direction in which the pair of sides of the yoke lid oppose each other. Accordingly, the bobbin (and consequently the solenoid coil) and the yoke lid are positioned relative to each other in the direction in which the pair of sides of the yoke lid oppose each other. As a result, in the operating period, the magnetic flux passing through the yoke, the yoke lid, the plunger, and the core is stable, and thereby the precision of adjusting the flow amount of the fluid is increased.

With an solenoid valve according to an embodiment, a direction in which the pair of sides of the yoke lid oppose each other substantially matches a direction in which the lock portion receives the external force about the movement path of the plunger.

Here, the "direction in which the external force is received" by the lock portion refers to the direction of a plane orthogonal to the movement path of the plunger.

With the solenoid valve according to the embodiment, the direction in which the pair of sides of the yoke lid oppose each other substantially matches the direction in which the external force is received by the lock portion about the movement path of the plunger. Accordingly, even if the lock portion receives the external force, the bobbin (and consequently the solenoid coil) and the yoke lid are positioned relative to each other in the direction in which the external force is received. Accordingly, even if the plunger and the valve body are replaced, a malfunction in which the bobbin (and consequently the solenoid coil) and the yoke lid are misaligned due to the external force is prevented. As a result, the precision of adjusting the flow amount of the fluid in the operating period is maintained.

An electronic blood pressure monitor according to one or more embodiments of the claimed invention is an electronic blood pressure monitor configured to measure blood pressure at a measurement site. According to one or more embodiments of the claimed invention, the blood pressure monitor includes a cuff to be attached at a measurement site, a pump for supplying air to the cuff, a solenoid valve according to one or more embodiments of the claimed invention, and a control unit configured to increase pressure in the cuff by supplying air to the cuff using the pump and reduce the pressure in the cuff by ejecting air through the solenoid valve from the cuff, and thereby control the pressure in the cuff.

The electronic blood pressure monitor according to one or more embodiments of the claimed invention includes the above-described solenoid valve in order to control the pressure in the cuff. Accordingly, in the solenoid valve, the plunger and the valve body can be replaced easily. Accordingly, various different flow rate properties can be easily realized without changing the entire solenoid valve. Also, maintenance can be easily performed on the interior of the solenoid valve.

As is evident from the foregoing description, with the solenoid valve according to one or more embodiments of the claimed invention, the plunger and the valve body can be replaced easily. Accordingly, various different flow rate properties can be easily realized without changing the entire solenoid valve. Also, maintenance can be easily performed on the interior.

Also, with the electronic blood pressure monitor according to one or more embodiments of the claimed invention, the plunger and the valve body can be replaced easily in the solenoid valve. Accordingly, various different flow rate properties can be easily realized without changing the entire solenoid valve. Also, maintenance can be easily performed on the interior of the solenoid valve.

DETAILED DESCRIPTION OF INVENTION

Hereinafter, embodiments of the claimed invention will be described in detail with reference to the drawings.

Figure 1:
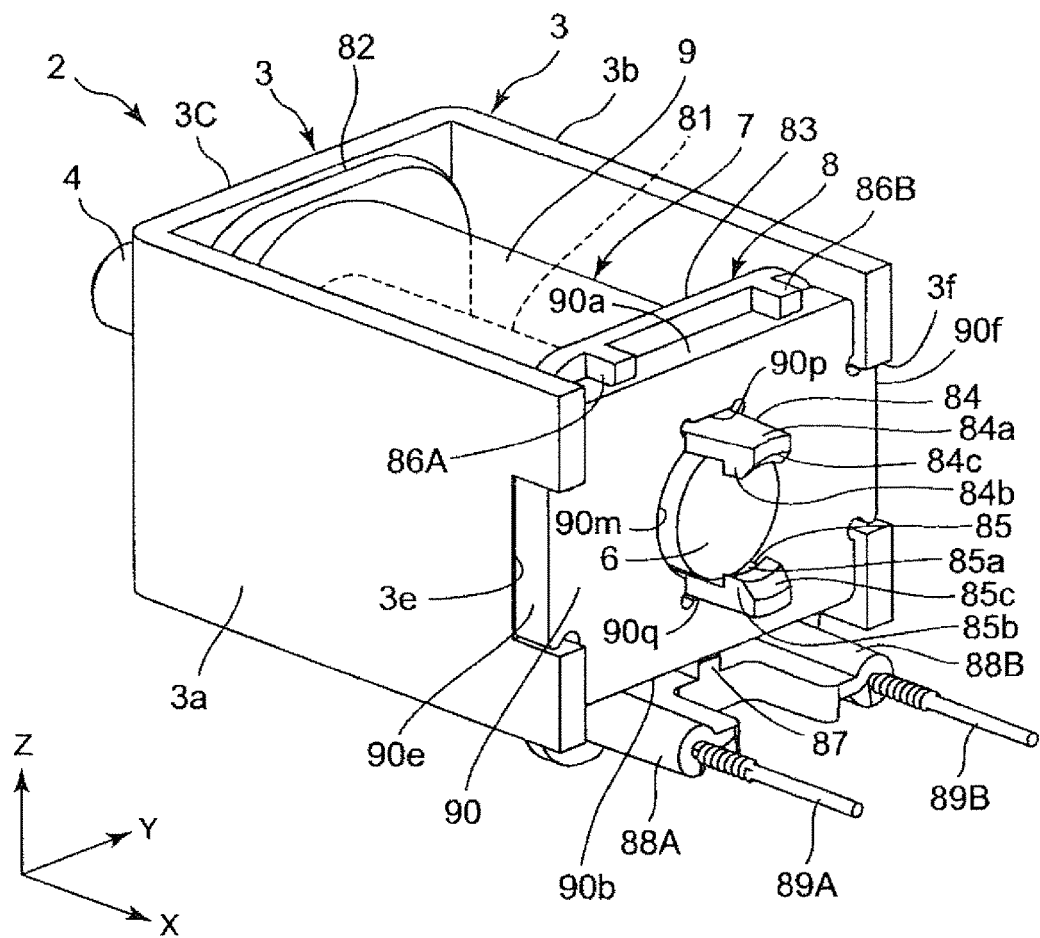
FIG. 1 is a perspective view showing an external appearance of a solenoid valve according to an embodiment of the claimed invention.
Figure 2:
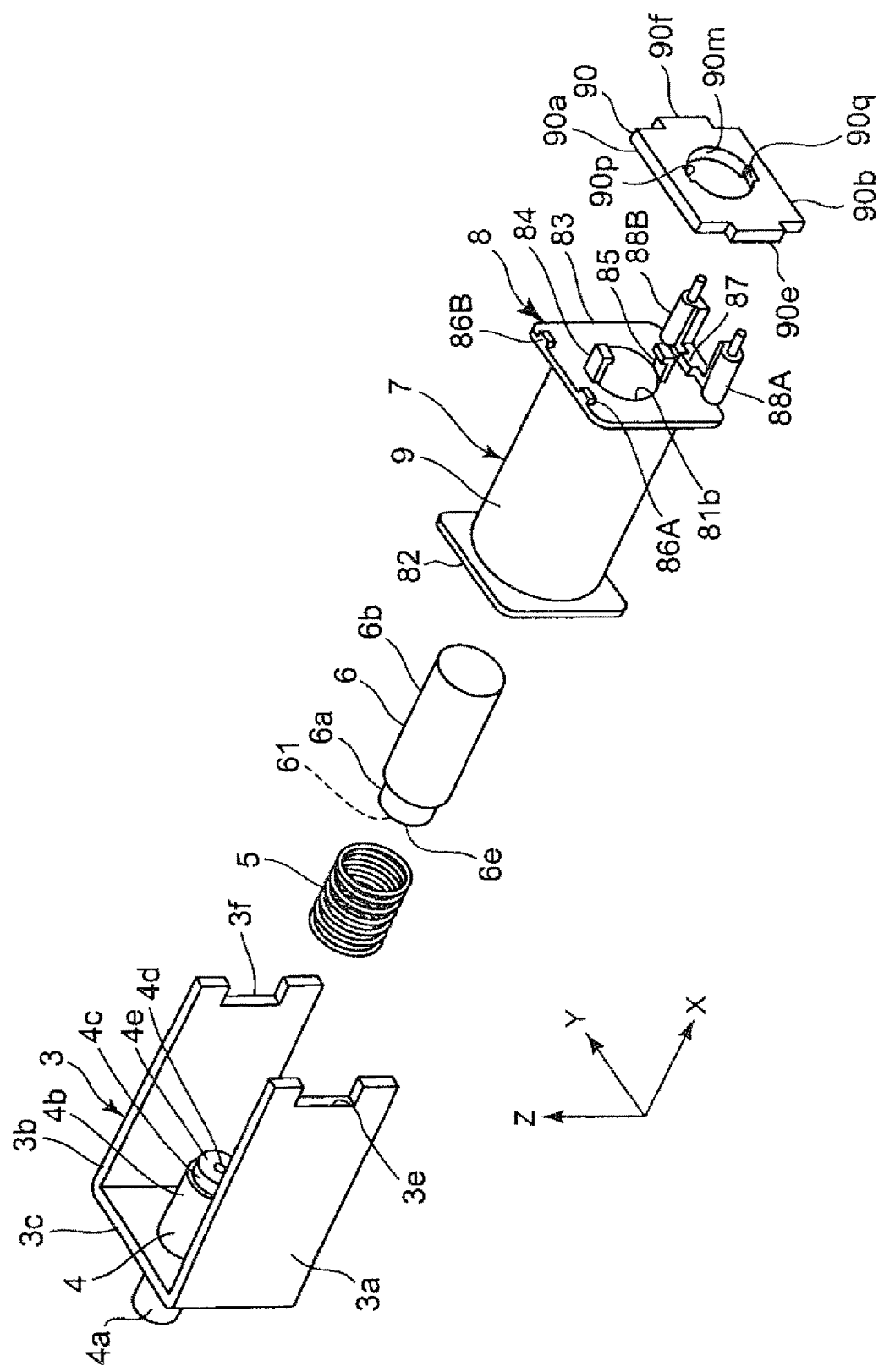
FIG. 2 is a diagram showing the solenoid valve in a disassembled state.

FIG. 1 shows a perspective view of an external appearance of a solenoid valve (indicated overall by reference numeral 2) according to an embodiment of the claimed invention. Also, FIG. 2 shows the solenoid valve 2 in a disassembled state. In order to facilitate understanding, orthogonal XYZ coordinates are shown in FIG. 1, FIG. 2, and in later-described FIG. 3. Hereinafter, the Z direction will sometimes be referred to as top and bottom or the vertical direction, and the Y direction will sometimes be referred to as left and right or the horizontal direction, for example, but this is merely for the sake of convenience in the description, and the Z direction is not limited to being vertical and the Y direction is not limited to being horizontal.

As can be understood from FIG. 2, the solenoid valve 2 includes a U-shaped yoke 3, a core 4 attached so as to penetrate a wall of the yoke 3, a coil spring 5 serving as a biasing portion, a rod-shaped plunger (movable iron core) 6, a coil unit 7, and a plate-shaped yoke lid 90 for closing the open end of the yoke 3.

The yoke 3 includes a central side wall 3c and two side walls 3a and 3b that are continuous with the central side wall 3c, and has an approximate U shape overall. Recessed portions 3e and 3f into which protrusions 90e and 90f of the yoke lid 90 are to fit are formed on the leading ends (open end) of the side walls 3a and 3b. A through hole 3w (e.g., see FIG. 4) is formed in the central side wall 3c. The core 4 fits into the through hole 3w and is thereby fixed.

As shown in FIG. 2, the core 4 has an approximately tubular shape overall. The core 4 includes a protruding portion 4a that fits in the through hole 3w of the yoke 3 and protrudes outward, a main portion 4b having an outer diameter that is larger than the outer diameter of the protruding portion 4a, and a spring receiving portion 4c having an outer diameter that is smaller than the outer diameter of the main portion 4b, in the stated order in the axial direction (X direction). A flow port 4d for allowing a fluid to flow therethrough is formed in the core 4 so as to penetrate in the axial direction from the protruding portion 4a to an end portion 4e on the side opposite thereto.

The plunger 6 has an approximately circular rod shape overall. The plunger 6 includes a spring receiving portion 6a having an outer diameter that is the same as that of the spring receiving portion 4c of the core 4, and a main portion 6b having an outer diameter that is the same as the outer diameter of the main portion 4b of the core 4, in the stated order in the axial direction (X direction). A valve body 61 composed of an elastic body such as rubber is attached to one end (end portion on the side opposing the flow port 4d of the core 4) 6e of the plunger 6. More specifically, a depression be (e.g., see FIG. 4) is provided on the one end 6e of the plunger 6, and the valve body 61 is fitted into the depression 6c.

As shown in FIG. 2, the coil spring 5 has a shape that extends in one direction (X direction) in the form of a spiral. The coil spring 5 has an inner diameter that is substantially equal to the outer diameter of the spring receiving portion 4c of the core 4 and the spring receiving portion 6a of the plunger 6, and has an outer diameter that is substantially equal to the outer diameter of the main portion 4b of the core 4 and the main portion 6b of the plunger 6. Accordingly, the coil spring 5 fits into the two spring receiving portions 4c and 6a and is compressed between the two main portions 4b and 6b so as to bias the plunger 6 in the direction of moving away from the core 4 (e.g., see FIG. 4).

As shown in FIG. 2, the coil unit 7 includes a bobbin 8, which is composed of a non-magnetic plastic material, and a solenoid coil 9 wound around the bobbin 8. The coil unit 7, and the configuration of the bobbin 8 in particular, will be described in detail later.

The yoke lid 90 has an approximately rectangular plate shape corresponding to the open end of the yoke 3. A pair of sides 90a and 90b corresponding to the top and bottom (Z direction) of the yoke lid 90 are formed so as to be flat. On the other hand, the protrusions 90e and 90f that are to fit into the recessed portions 3e and 3f of the yoke 3 are formed on the pair of sides corresponding to the left and right (Y direction). An approximately circular through hole 90m is formed in the center of the yoke lid 90.

More specifically, the through hole 90m has an approximately circular shape that substantially corresponds to the cross-section of the plunger 6. Extended regions 90p and 90q that are extended in order to allow passage of lock portions 84 and 85 (in particular, later-described arm portions 84a and 85a) of the bobbin 8 are formed at the top and bottom (Z direction) of the through hole 90m. The diameter of the through hole 90m (the portion not including the extended regions 90p and 90q) is set to be substantially equal to the outer diameter of the main portion 6b of the plunger 6.

Figure 3:
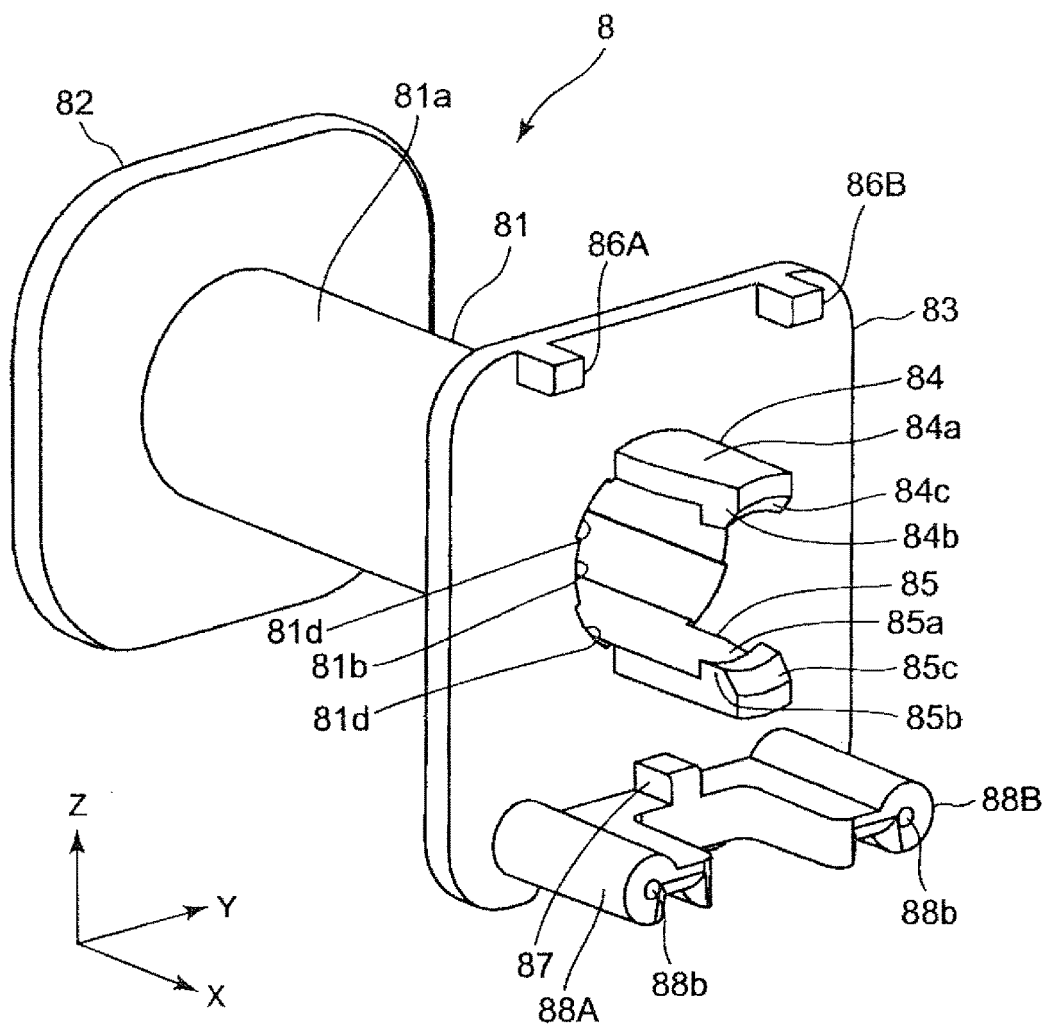
FIG. 3 is a perspective view showing a bobbin included in the solenoid valve.

As shown in detail in FIG. 3, the bobbin 8 includes a tubular main portion 81 and plate-shaped end plates 82 and 83 provided on one end (−X-side end portion) and the other end (+X-side end portion) in the axial direction (X direction) of the main portion 81. The end plates 82 and 83 are each disposed orthogonally to the central axis of the main portion 81. The solenoid coil 9 is wound around an external circumferential face 81a of the main portion 81 between the end plates 82 and 83. The main portion 81 and end plates 82 and 83 form a main body portion of the bobbin 8 (in the complete state shown in FIG. 1, the bobbin 8 is housed in a casing created by the yoke 3 and the yoke lid 90).

The main portion 81 includes, in its interior, an approximately circular through hole 81b that extends in the axial direction (X direction). Several extended regions 81d, 81d, that are extended in order to allow the fluid to flow through are formed in the through hole 81b. The extended regions 81d, 81d, . . . are formed at a certain angular interval in the circumferential direction of the through hole 81b and extend in the X direction. The diameter of the through hole 81*b* (the portion not including the extended regions 81*d*, 81*d*, . . . ) has an outer diameter that is substantially equal to the outer diameter of the plunger 6 so that the plunger 6 can be slid therein.

The +X-side end plate 83 has lock portions 84 and 85 serving as first extended portions that extend or protrude to the +X side, protrusions 86A and 86B serving as second extended portions, a protrusion 87 serving as a third extended portion, and terminal covers 88A and 88B. The bobbin 8 is formed integrally with the elements 84, 85, 86A, 86B, 87, 88A, and 88B using a non-magnetic plastic material. Accordingly, it is not necessary to bother to increase the number of components to provide the elements 84, 85, 86A, 86B, 87, 88A, and 88B. As a result, it is possible to avoid a rise in the manufacturing cost of the solenoid valve 2.

The lock portion 84 has an arm portion 84*a* that extends from a position adjacent to the top of the through hole 81*b* to the +X side on the +X-side face of the end plate 83, and a hook portion 84*b* that extends to the −Z side substantially orthogonally from the leading end of the arm portion 84*a* and has a cut-off leading end. On the other hand, vertically symmetrically with the lock portion 84, the lock portion 85 has an arm portion 85*a* that extends from a position adjacent to the bottom of the through hole 81*b* to the +X side on the +X-side face of the end plate 83, and a hook portion 85*b* that extends to the +Z side substantially orthogonally from the leading end of the arm portion 85*a* and has a cut-off leading end.

The leading end side of the arm portion 84*a* of the lock portion 84 can bend to the +Z side due to an external force, although this will be described in detail later. On the other hand, the leading end side of the arm portion 85*a* of the lock portion 85 can bend to the −Z side due to an external force.

Also, tapered surfaces 84*c* and 85*c* that are open toward the outside (in the +X direction) are provided on sides opposite to the sides that abut against the plunger 6 of the hook portions 84*b* and 85*b*. The tapered surfaces 84*c* and 85*c* are each curved in a circular arc shape along the circumferential direction of the through hole 81*b*.

The protrusions 86A and 86B are disposed on the left and right (Y direction) along the upper edge of the end plate 83 and extend toward the +X side. The protrusion 87 is disposed in the center with respect to the left and right (Y direction) in the lower portion of the end plate 83 and extend toward the +X side. The interval in the vertical direction (Z direction) between the protrusions 86A and 86B and the protrusion 87 substantially matches the dimension in the vertical direction of the yoke lid 90 (the distance between the pair of sides 90*a* and 90*b* that vertically oppose each other). Accordingly, in a state in which the through hole 81*b* of the bobbin 8 and the through hole 90*m* of the yoke lid 90 are aligned, the yoke lid 90 is fit between the protrusions 86A and 86B and the protrusion 87. In this example, the terminal covers 88A and 88B are disposed on the left and right (Y direction) along the lower edge of the end plate 83 and extend toward the +X side. In this example, the height (Z-direction position) of the terminal covers 88A and 88B on the +X-side surface of the end plate 83 is set to be slightly lower than the height of the protrusion 87, but it may be the same as the height of the protrusion 87.

Note that when the solenoid coil 9 has been wound around the bobbin 8 so as to form the coil unit 7, lead terminals 89A and 89B (see FIG. 1) that are continuous with the solenoid coil 9 are passed through lead holes 88*b* and 88*b* in the terminal covers 88A and 88B.

The solenoid valve 2 is assembled by putting together the elements shown in FIG. 2 in the X direction. For example, one end (−X-side end portion) of the coil spring 5 is fit onto the spring receiving portion 4*c* of the core 4, which is attached to the yoke 3. Also, the plunger 6 is accommodated in the through hole 81*b* of the bobbin 8 of the coil unit 7 (around which the solenoid coil 9 has been wound in advance). The bobbin 8 in this state is accommodated in the yoke 3, and the spring receiving portion 6*a* of the plunger 6 is fit into the other end (+X-side end portion) of the coil spring 5. Also, the yoke lid 90 is brought near the end plate 83 of the bobbin 8 so that the lock portions 84 and 85 of the end plate 83 pass through the through hole 90*m* of the yoke lid 90 (or more accurately, the expanded regions 90*p* and 90*q*), and the yoke lid 90 is fit between the protrusions 86A and 86B and the protrusion 87 of the end plate 83. Also, the protrusions 90*e* and 90*f* of the yoke lid 90 are fit into the recessed portions 3*e* and 3*f* on the open end of the yoke 3. Finally, the yoke lid 90 is fixed to the yoke 3 by fastening. Accordingly, the solenoid valve 2 shown in FIG. 1 is complete.

The yoke 3, the core 4, the plunger 6, and the yoke lid 90 are composed of magnetic materials and can form a magnetic circuit when operating. In particular, the yoke 3 and the yoke lid 90 are composed of cold-rolled steel plates with mechanical strength, and constitute the casing (hereinafter referred to as "casing 3, 90" where appropriate) of the solenoid valve 2.

Figure 4:
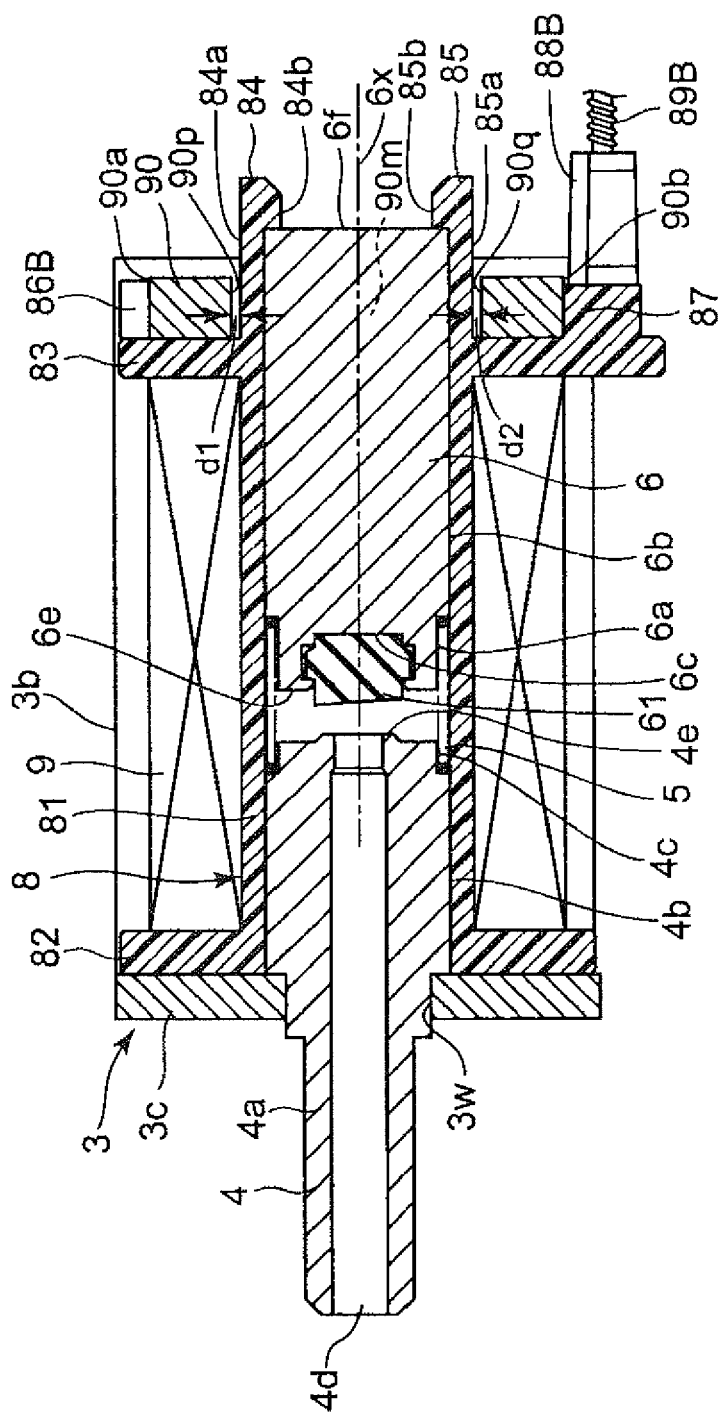
FIG. 4 is a diagram schematically showing a cross-section of the solenoid valve in a non-operating period.

FIG. 4 schematically shows a cross section taken parallel to the ZX plane in FIGS. 1 to 3 of the completed solenoid valve 2 (non-operating period) (the same applies in FIGS. 5 to 9, which will be described later). In the completed state, the flow port 4*d* of the core 4 and the valve body 61 attached to the one end 6*e* of the plunger 6 oppose each other in the main portion 81 of the bobbin 8. The core 4 is fixed to the yoke 3, whereby it is stationary with respect to the main portion 81 of the bobbin 8. The plunger 6 can slide in the axial direction in the main portion 81 of the bobbin 8. Note that in FIG. 4 (and in later-described FIGS. 5 to 9), a path 6*x* on which the plunger 6 moves (referred to as "plunger movement path") is represented by a single-dot chain line that extends in the longitudinal direction (i.e., the axial direction) of the plunger 6 (in actuality, the plunger movement path 6*x* has a size that corresponds to the outer diameter of the plunger 6). When compressed between the main portion 4*b* of the core 4 and the main portion 6*b* of the plunger 6, the coil spring 5 biases the plunger 6 in the direction of moving away from the core 4.

Also, the hook portions 84*b* and 85*b* of the lock portions 84 and 85 extend from the leading ends of the arm portions 84*a* and 85*a* toward the plunger movement path 6*x*. Also, the arm portions 84*a* and 85*a* pass through the through hole 90*m* so as to extend outward from the casing 3, 90 on the plunger movement path 6*x* and the leading end sides thereof can bend in directions of moving away from the plunger movement path 6*x* due to external forces. According to this, the lock portions 84 and 85 can be elastically deformed due to the external forces so as to allow separation of the plunger 6 and the valve body 61 from the casing 3, 90.

Also, in the completed state, with respect to the orientation in which at least the arm portions 84*a* and 85*a* are moved away from the plunger movement path 6*x* (the vertical direction in FIG. 4), gaps d1 and d2 are respectively provided between the arm portions 84*a* and 85*a* and faces opposing the arm portions 84*a* and 85*a* of the extended regions 90*p* and 90*q*.

Also, the protrusions 86A and 86B provided on the upper side of the end plate 83 of the bobbin 8 and the projection 87 provided on the lower side come into contact with the pair of opposing sides 90a and 90b of the yoke lid 90 and extend outward from the casing 3, 90, parallel with the plunger movement path 6x.

As shown in FIG. 4, in a non-operating period during which the solenoid coil 9 is in a non-energized state, the valve body 61 provided on the one end 6e of the plunger 6 is located away from the flow port 4d due to the biasing force applied by the coil spring 5. The other end 6f of the plunger 6 protrudes outward from the casing 3, 90 through the through hole 90m so as to abut against the hook portions 84b and 85b of the lock portions 84 and 85 disposed outside of the casing 3, 90, and is thereby locked (this state of the lock portions 84 and 85 is referred to as a "closed state").

Figure 5:
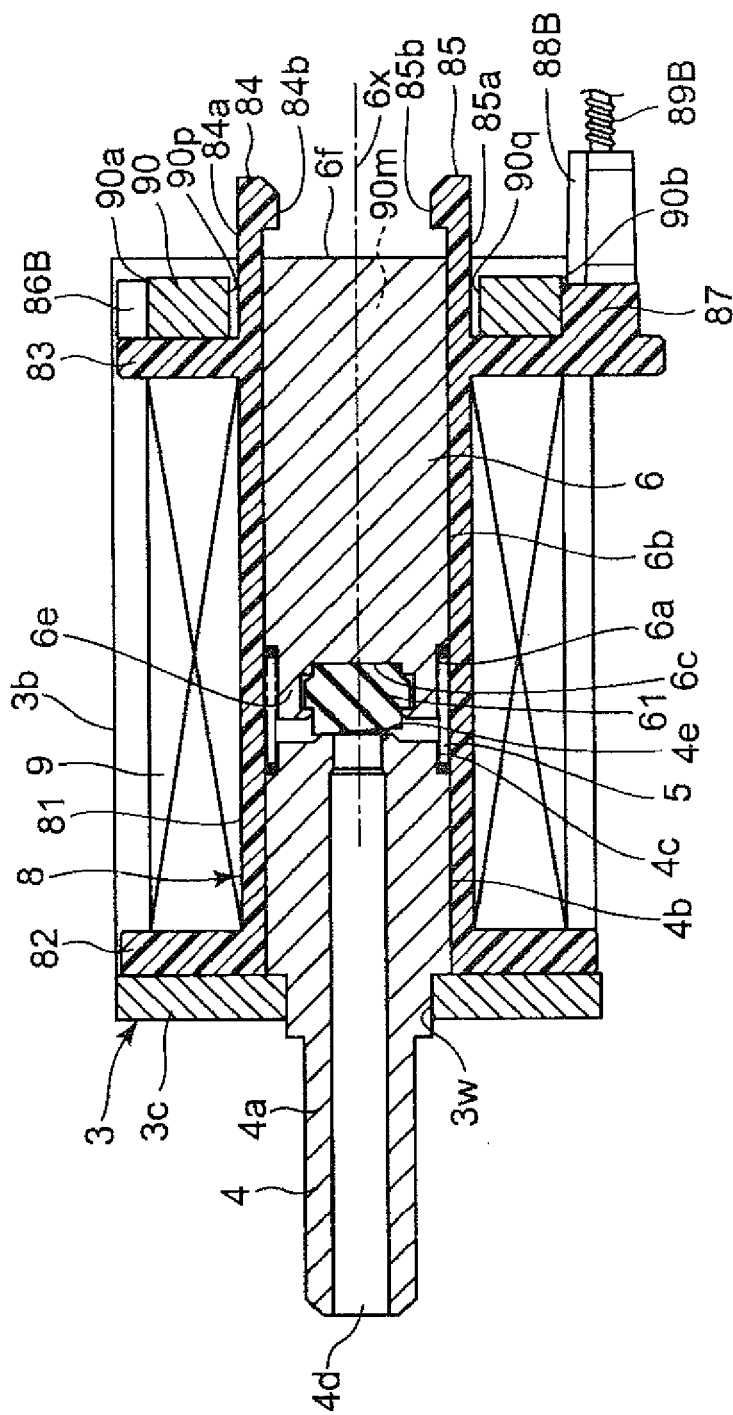
FIG. 5 is a diagram schematically showing a cross-section of the solenoid valve in an operating period.

As shown in FIG. 5, in an operating period during which the solenoid coil 9 is in an energized state, the plunger 6 and the valve body 61 are moved inside the bobbin 8 against the biasing force applied by the coil spring 5 due to the magnetic force generated by the solenoid coil 9. Accordingly, the flow amount of the fluid flowing through the flow port 4d is adjusted.

If disassembly is needed in order to realize various different flow amount properties, the plunger 6 and the valve body 61 are replaced using the following procedures in i) Separation and ii) Insertion.

i) Separation

Figure 6:
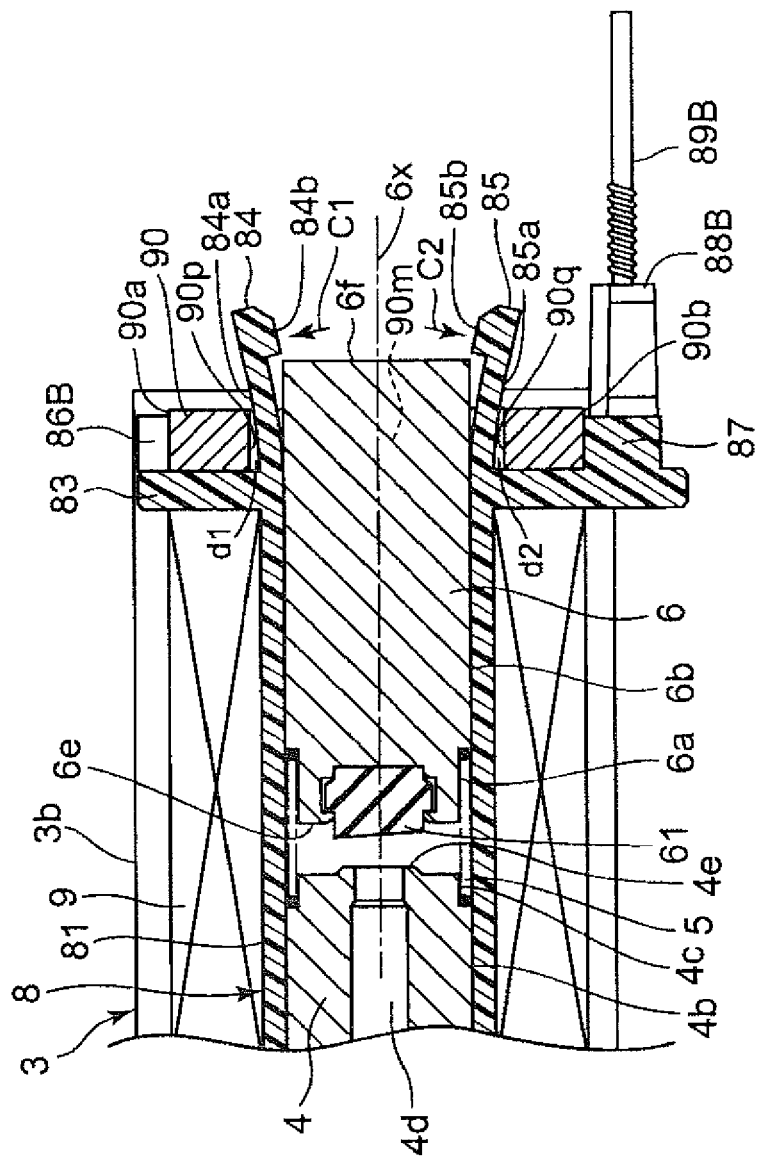
FIG. 6 is a cross-sectional view showing a lock portion in an open state in the solenoid valve.

As shown in FIG. 6, in a non-operating period during which the solenoid coil 9 is in the non-energized state, the lock portions 84 and 85 are elastically deformed by external forces C1 and C2 so as to be put into a state in which the plunger 6 can be allowed to pass through (this is referred to as an "open state"). Specifically, the arm portion 84a is bent upward and the arm portion 85a is bent downward by the external forces C1 and C2 applied by a person's fingers, for example. That is to say, the arm portions 84a and 85a are bent in directions of moving away from the plunger movement path 6x. Accompanying this, the hook portions 84b and 85b are moved away from the plunger movement path 6x and the lock portions 84 and 85 enter the open state.

Here, in the solenoid valve 2, the gaps d1 and d2 are respectively provided between the arm portions 84a and 85a and the faces opposing the aim portions 84a and 85a of the expanded regions 90p and 90q, with respect to at least the direction in which the arm portions 84a and 85a move away from the plunger movement path 6x (the vertical direction). Accordingly, when the arm portions 84a and 85a are bent in directions of moving away from the plunger movement path 6x by the external forces C1 and C2, the arm portions 84a and 85a easily bend from bases that are continuous with the end plate 83 of the bobbin 8, while reducing the gaps d1 and d2, without coming into contact with the faces opposing the arm portions 84a and 85a of the expanded regions 90p and 90q. Accordingly, the lock portions 84 and 85 can be put into the open state using smaller external forces C1 and C2. As a result, a situation in which the arm portions 84a and 85a break during deformation for putting the lock portions 84 and 85 into the open state can be prevented.

Figure 7:
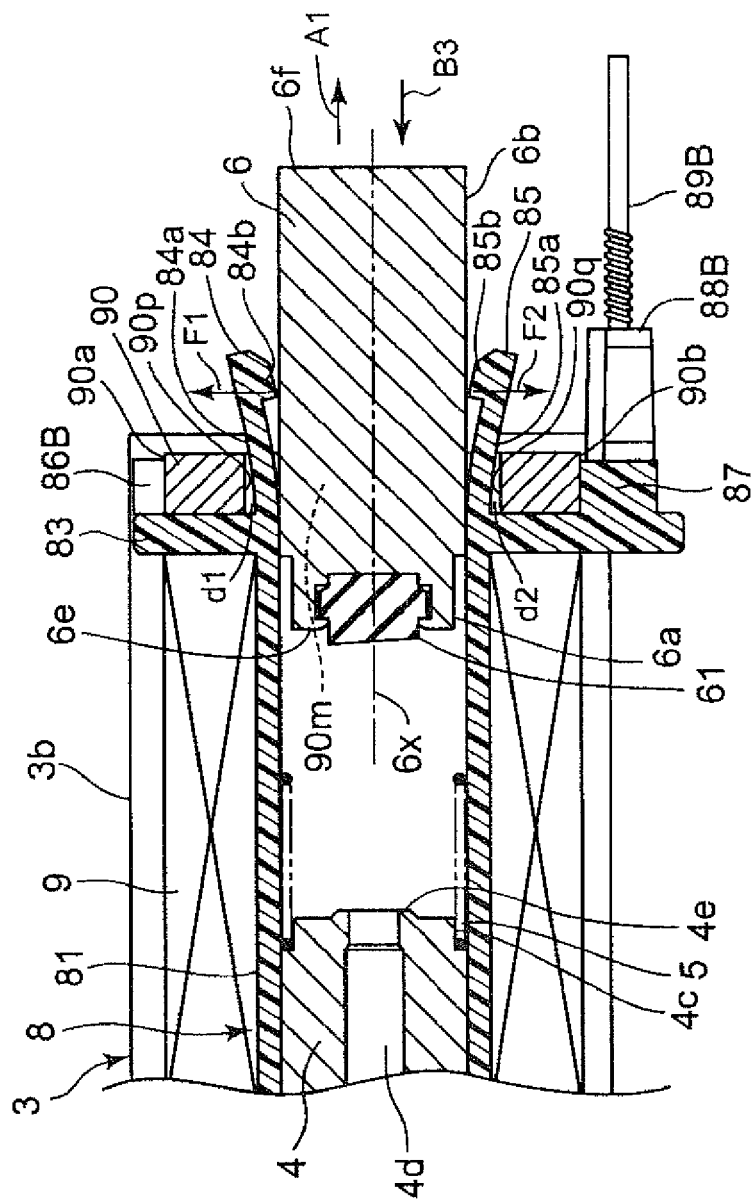
FIG. 7 is a diagram showing a mode for when a plunger and a valve body are separated from (or inserted into) a casing in the solenoid valve.

Next, when the plunger 6 is pulled out along the plunger movement path 6x in the direction indicated by arrow A1 in FIG. 7, the hook portions 84b and 85b come into contact with the external circumferential face of the main portion 6b of the plunger 6, and even if the initial external forces C1 and C2 are removed, forces F1 and F2 that bend the arm portions 84a and 85a in directions of moving away from the plunger movement path 6x are received from the external circumferential face. Accordingly, the lock portions 84 and 85 maintain the open state. In view of this, with the open state maintained, the plunger 6 and the valve body 61 are taken out of the casing 3, 90 through the lock portions 84 and 85 in the open state.

Thus, it is possible to separate the plunger 6 and the valve body 61 from the casing 3, 90 (i.e., the bobbin 8) through the lock portions 84 and 85 in the open state.

ii) Insertion

Instead of the original plunger 6 described above, a new plunger 6 (described using the same reference numeral as the original plunger 6 for the sake of simplicity) with a new valve body 61 provided on one end 6e is inserted into the casing 3, 90 (or more accurately, into the bobbin 8) as follows. Note that after the original plunger 6 and valve body 61 are separated from the casing 3, 90, the external forces on the lock portions 84 and 85 are removed temporarily, and the lock portions 84 and 85 are in the closed state.

Figure 8:
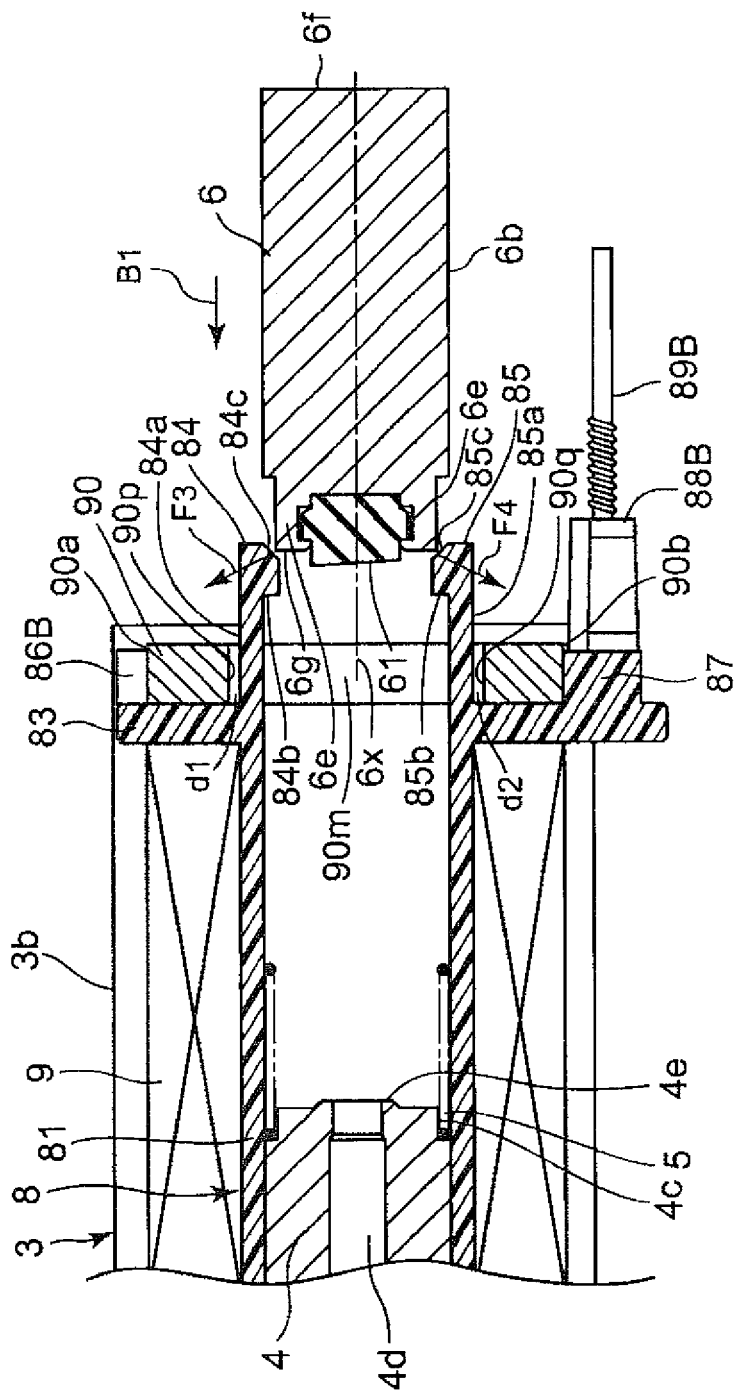
FIG. 8 is a diagram showing a state in which a new plunger provided with a valve body at one end is about to be inserted into the solenoid valve.

First, the new plunger 6 provided with the valve body 61 on the one end 6e is brought near the lock portions 84 and 85 along the plunger movement path 6x in the direction indicated by arrow B1 in FIG. 8.

Here, with the solenoid valve 2, the tapered surfaces 84c and 85c, which are open toward the outside of the casing 3, 90, are provided on the hook portions 84b and 85b. Accordingly, when the new plunger 6 is to be inserted into the interior from the outside of the casing 3, 90 along the movement path 6x, an edge 6g of the one end 6e (end portion on which the valve body 61 is provided) of the new plunger 6 abuts against the tapered surfaces 84c and 85c of the hook portions 84b and 85b. According to this, from the edge 6g of the one end 6e of the new plunger 6, the lock portions 84 and 85 (the hook portions 84b and 85b thereof) receive, as the external forces, forces F3 and F4 that bend the arm portions 84a and 85a in directions of moving away from the plunger movement path 6x. Next, when the new plunger 6 is pushed into the interior of the casing 3, 90, the arm portions 84a and 85a bend in directions of moving away from the plunger movement path 6x (the vertical direction), the hook portions 84b and 85b partially move away from the plunger movement path 6x, and the lock portions 84 and 85 partially enter the open state. As indicated by the arrow B2 in FIG. 9, when the new plunger 6 is pushed further into the interior of the casing 3, 90, the hook portions 84b and 85b come into contact with the external circumferential face of the spring receiving portion 6a of the new plunger 6 and receive, from the external circumferential face, forces F5 and F6 that bend the arm portions 84a and 85a in directions of moving away from the plunger movement path 6x. Accordingly, the lock portions 84 and 85 maintain the partial open state.

Figure 9:
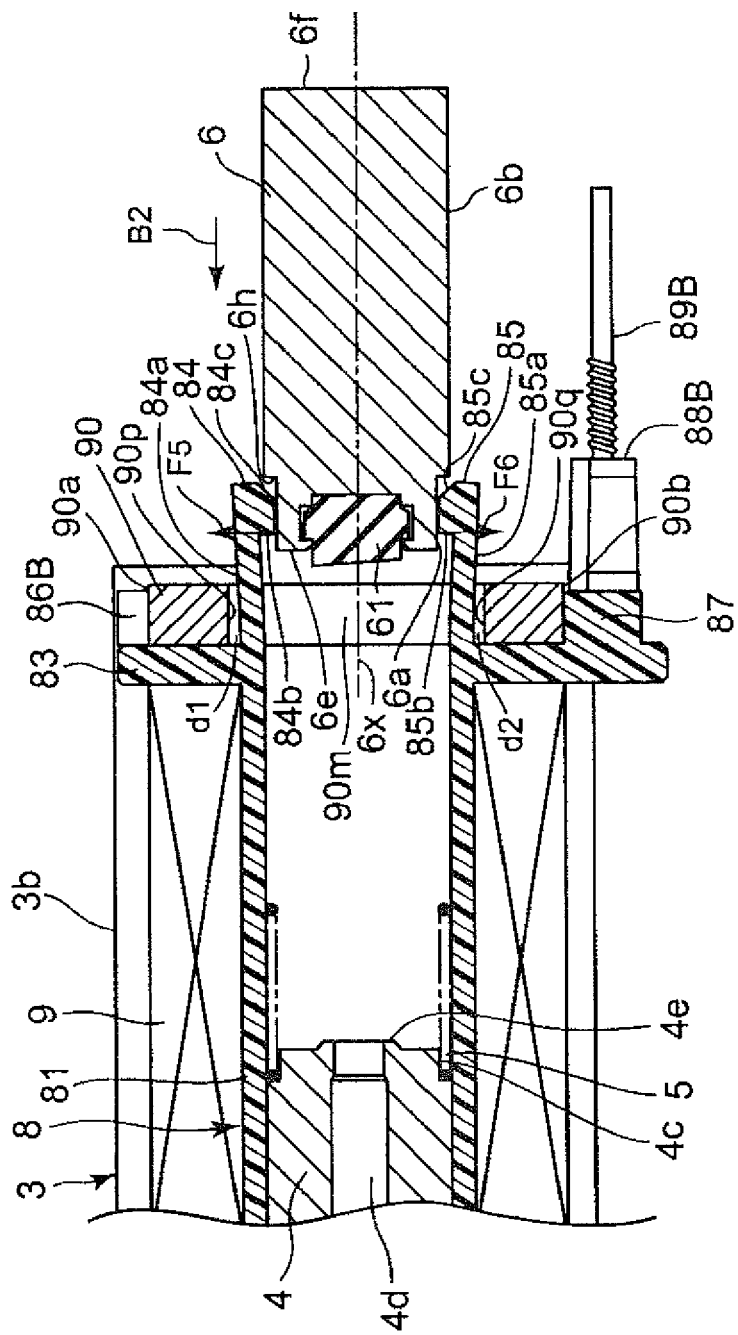
FIG. 9 is a diagram showing a state in which a new plunger provided with a valve body at one end is being inserted into the solenoid valve.

When the new plunger 6 is pushed further into the interior of the casing 3, 90 from the state shown in FIG. 9, the edge 6h of the main portion 6b of the new plunger 6 abuts against the tapered surfaces 84c and 85c of the hook portions 84b and 85b. According to this, from the edge 6h of the main portion 6b of the new plunger 6, the lock portions 84 and 85 (the hook portions 84b and 85b thereof) receive, as the external forces, forces (not shown) that bend the arm portions 84a and 85a in directions of moving away from the plunger movement path 6x. Next, as indicated by arrow B3 in FIG. 7, when the new plunger 6 is pushed further into the interior of the casing 3, 90, the arm portions 84a and 85a further bend in the directions of moving away from the plunger movement path 6x, the hook portions 84b and 85b come into contact with the external circumferential face of the main portion 6b of the new plunger 6, and the forces F1 and F2 that bend the arm portions 84a and 85a in directions of moving away from the plunger movement path 6x are received from the external circumferential face. Accordingly, the lock portions 84 and 85 maintain the complete open state. While the complete open state is maintained, the new plunger 6 and valve body 61 are inserted into the casing 3, 90 through the lock portions 84 and 85 in the open state and the through hole 90m.

When the new plunger 6 and valve body 61 are completely inserted into the casing 3, 90, the external forces F1 and F2 on the lock portions 84 and 85 are removed. As a result, the lock portions 84 and 85 return to their original shape and enter the closed state, in which passage of the newly-inserted plunger 6 is prohibited. That is to say, in a non-operating period, the other end 6f (the end portion on the side opposite to the one end 6e provided with the valve body 61) of the newly-inserted plunger 6 protrudes outward of the casing 3, 90 through the through hole 90m, abuts against the lock portions 84 and 85 (the hook portions 84b and 85b thereof) and is thereby locked.

If the new plunger 6 and valve body 61 are thus inserted, the lock portions 84 and 85 enter the open state by receiving the external force F from the new plunger 6 that is pushed in. Accordingly, there is no need to apply a separate external force F to the lock portions 84 and 85, which is convenient.

Thus, with the solenoid valve 2, the plunger 6 and the valve body 61 can be replaced easily. Accordingly, by changing the angle and hardness of the surface opposing the flow port 4d of the new valve body 61 with respect to the valve body 61 that was used before being replaced, various different flow amount properties can be realized easily without changing the entire solenoid valve 2. Also, maintenance can be easily performed on the interior. Note that it is possible to re-use the plunger 6 itself (metal portion) and replace only the valve body 61.

With the solenoid valve 2, the tapered surfaces 84c and 85c that are open toward the outside (in the +X direction) are provided on the hook portions 84b and 85b of the pair of lock portions 84 and 85, as shown in FIG. 3. The tapered surfaces 84c and 85c are each curved in a circular arc shape along the circumferential direction of the through hole 81b. Accordingly, as shown in FIGS. 8 and 9, when the new plunger 6 is pushed into the interior of the casing 3, 90, the edge 6g of the one end 6e of the new plunger 6 is partially surrounded by the tapered surfaces 84c and 85c with respect to the circumferential direction. As a result, the one end 6e of the new plunger 6 is less likely to come out from between the hook portions 84b and 85b of the lock portions 84 and 85, and the new plunger 6 can be easily pushed into the interior of the casing 3, 90.

Also, as shown in FIG. 6 for example, with the solenoid valve 2, the protrusions 86A and 86B provided on the upper side of the end plate 83 of the bobbin 8 and the protrusion 87 provided on the lower side come into contact with the pair of opposing sides 90a and 90b of the yoke lid 90 and extend outward of the casing 3, 90, parallel with the plunger movement path 6x. That is to say, the protrusions 86A and 86B provided on the upper side and the protrusion 87 provided on the lower side sandwich the yoke lid 90 in the direction in which the pair of sides 90a and 90b of the yoke lid 90 oppose each other (the vertical direction in FIG. 6). Accordingly, the bobbin 8 (and consequently, the solenoid coil 9) and the yoke lid 90 are positioned relative to each other in the direction in which the pair of sides 90a and 90b of the yoke lid 90 oppose each other. As a result, in an operating period, the magnetic flux passing through the yoke 3, the yoke lid 90, the plunger 6, and the core 4 is stable, and the precision of adjusting the flow amount of the fluid is increased.

Moreover, the direction in which the pair of sides 90a and 90b of the yoke lid 90 oppose each other (the vertical direction in FIG. 6) matches the direction in which the lock portions 84 and 85 receive the external forces (C1, C2, etc.) about the plunger movement path 6x, for replacing the plunger 6 and the valve body 61. Accordingly, even if the plunger 6 and the valve body 61 are replaced, a malfunction in which the positions of the bobbin 8 (and consequently, the solenoid coil 9) and the yoke lid 90 are misaligned due to the external forces is prevented. As a result, the precision of adjusting the flow amount of the fluid in the operating period is maintained.

With the solenoid valve 2, the lock portion was composed of two sets, namely a set 84 composed of the arm portion 84a and the hook portion 84b, and a set 85 composed of the arm portion 85a and the hook portion 85h. Accordingly, in a non-operating period, the strength of locking the other end 6f of the plunger 6 is increased in comparison to a case where the lock portion is composed of one set. Also, even if the lock portion of a set (e.g., arm portion 84a) breaks during deformation for putting the lock portions 84 and 85 in the open state, in the non-operating state, the other end 6f of the plunger 6 can be locked by the lock portion of the remaining set (in this example, lock portion 85). Note that it is possible to provide only one set or three or more sets of lock portions composed of an arm portion and a hook portion.

Figure 10:
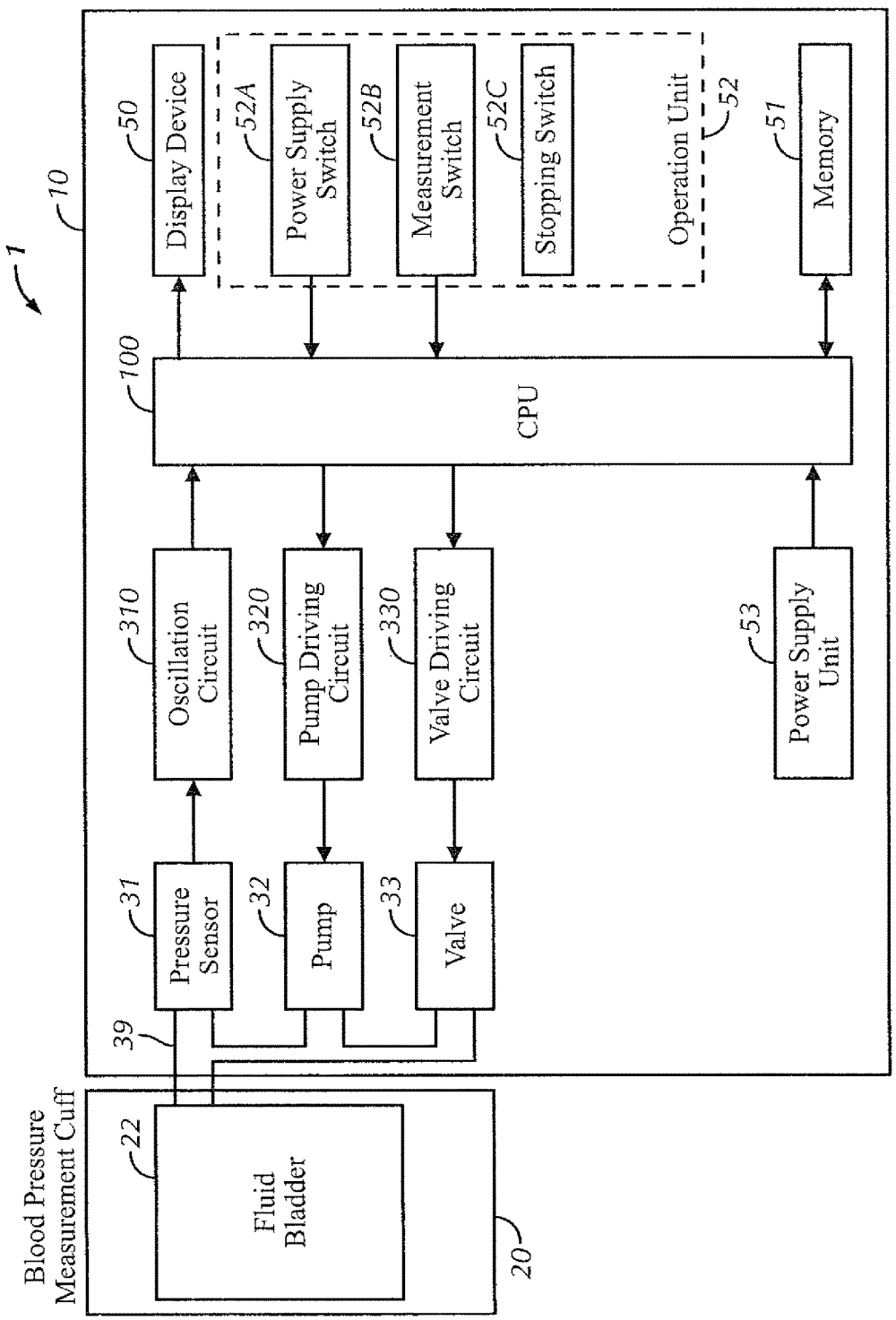
FIG. 10 is a diagram showing a block configuration of an electronic blood pressure monitor equipped with the solenoid valve, according to an embodiment of the claimed invention.

FIG. 10 shows an overall block configuration of an electronic blood pressure monitor (indicated overall by reference numeral 1) according to an embodiment of the claimed invention. The blood pressure monitor 1 includes a cuff 20, a main body 10, and a CPU (Central Processing Unit) 100 serving as a control unit, a display device 50, a memory 51 serving as a storage unit, an operation unit 52, a power supply unit 53, a pump 32, a valve 33 composed of the above-described solenoid valve 2, and a pressure sensor 31, which are mounted in the main body 10. Also, the main body 10 includes an oscillation circuit 310 that converts an output from the pressure sensor 31 into a frequency, a pump driving circuit 320 that drives the pump 32, and a valve driving circuit 330 that drives the valve 33, all of which are mounted in the main body 10.

The display device 50 includes a display, an indicator, and the like, and displays predetermined information in accordance with control signals from the CPU 100.

The operation unit 52 includes a power supply switch 52A that receives input of an instruction to turn on or turn off the power supply unit 53, a measurement switch 52B for receiving an instruction to start measurement of blood pressure, and a stopping switch 52C for receiving an instruction to stop measurement. The switches 52A, 52B, and 52C input operation signals corresponding to an instruction given by a user to the CPU 100.

The memory 51 stores data for programs for controlling the blood pressure monitor 1, data used for controlling the blood pressure monitor 1, setting data for setting various functions of the blood pressure monitor 1, data on results of measuring the blood pressure value, and the like. Also, the memory 51 is used as a working memory or the like for when a program is executed.

The CPU 100 functions as a cuff pressure control unit in accordance with a program for controlling the blood pressure monitor 1 that is stored in the memory 51, and performs control for driving the pump 32 and the valve 33 in response to operation signals from the operation unit 51. Also, the CPU 100 calculates the blood pressure values and controls the display device 50 and the memory 51 based on signals from the pressure sensor 31.

The power supply unit 53 supplies power to the CPU 100, the pressure sensor 31, the pump 32, the valve 33, the display device 50, the memory 51, the oscillation circuit 310, the pump driving circuit 320, and the valve driving circuit 330.

The pump 32 supplies air to a fluid bladder 22 contained in the cuff 20 in order to increase the pressure in the fluid bladder 22 (cuff pressure). The valve 33 is opened and closed in order to discharge or seal the air in the fluid bladder 22 and thereby control the cuff pressure. The pump driving circuit 320 drives the pump 32 based on a control signal provided from the CPU 100. The valve driving circuit 330 opens and closes the valve 33 based on a control signal provided from the CPU 100.

The pressure sensor 31 and the oscillation circuit 310 function as a pressure detection unit that detects the pressure in the cuff. The pressure sensor 31 is a piezoresistive pressure sensor, for example, and is connected via a cuff air tube 39 to the pump 32, the valve 33, and the fluid bladder 22 contained in the cuff 20. In this example, the oscillation circuit 310 oscillates based on an electric signal value that is from the pressure sensor 31 and is based on a change in electric resistance due to the piezoresistive effect, and outputs a frequency signal having a frequency corresponding to the electric signal value of the pressure sensor 31 to the CPU 100.

If blood pressure is to be measured in accordance with a common oscillometric method, the following operation is generally performed. That is, the cuff is wrapped around a measurement site (arm, etc.) of the measurement subject in advance, and during measurement, the pump and valve are controlled so as to increase the cuff pressure so that it is higher than the systolic blood pressure, and gradually reduce the cuff pressure thereafter. In the process of the pressure decreasing, the cuff pressure is detected by the pressure sensor, and changes in the arterial volume that occur in the artery at the measurement site are retrieved as a pulsewave signal. The systolic blood pressure and the diastolic blood pressure are calculated based on changes (mainly rising edges and falling edges) in the amplitude of the pulsewave signal that accompany changes in the cuff pressure at this time.

Figure 11:
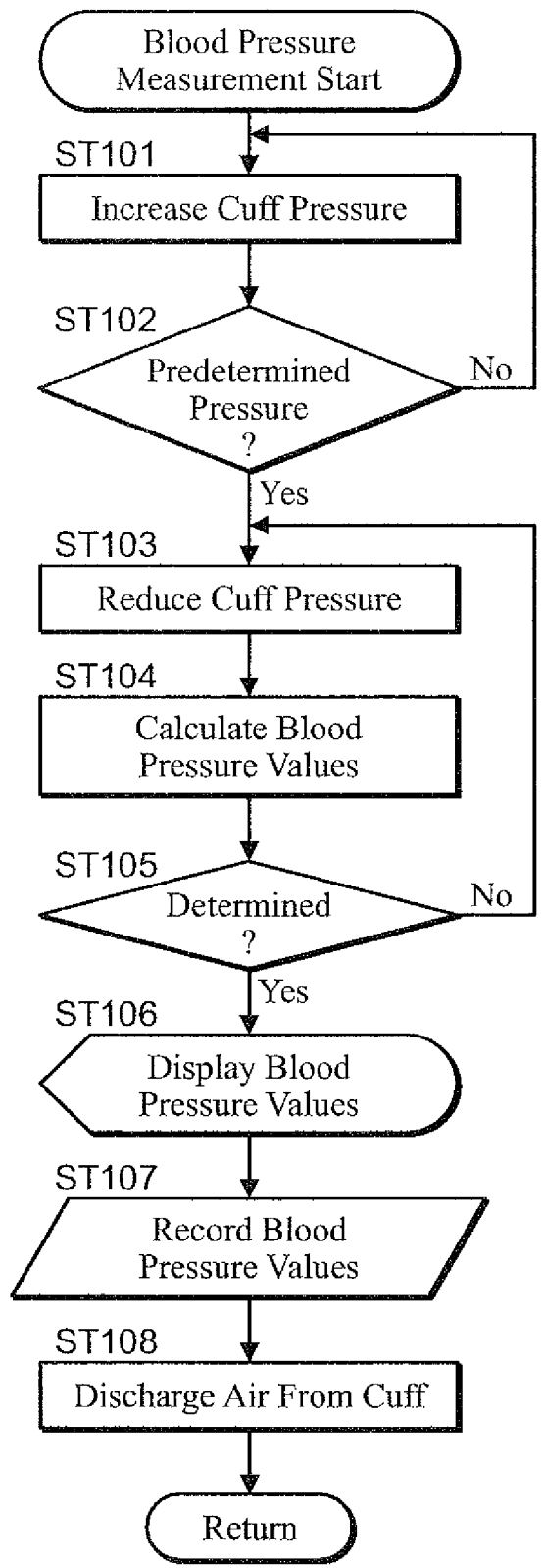
FIG. 11 is a diagram showing an operation flow of the electronic blood pressure monitor.

With the blood pressure monitor 1, the blood pressure values of a measurement subject are measured by the CPU 100 using an oscillometric method in accordance with the flow in FIG. 11.

Specifically, when the measurement switch 52B is pressed while the power supply switch 52A is on, the blood pressure monitor 1 starts blood pressure measurement, as shown in FIG. 11. When blood pressure measurement is started, the CPU 100 initializes the memory region for processing, and outputs a control signal to the valve driving circuit 330. Based on the control signal, the valve driving circuit 330 opens the valve 33 so as to discharge the air in the fluid bladder 22 of the cuff 20. Next, control for adjusting the pressure sensor 31 to 0 mmHg is performed.

When blood pressure measurement is started, the CPU 100 first closes the valve 33 via the valve driving circuit 330 and then drives the pump 32 via the pump driving circuit 320, thereby performing control for sending air to the fluid bladder 22. Accordingly, the fluid bladder 22 is inflated and the cuff pressure gradually increases (step ST101).

When the cuff pressure is increased to a predetermined pressure (YES in step ST102), the CPU 100 stops the pump 32 via the pump driving circuit 320, and then performs control for gradually opening the valve 33 via the valve driving circuit 330. Accordingly, the fluid bladder 22 is deflated and the cuff pressure gradually decreases (step ST103).

Here, the predetermined pressure is a pressure that is sufficiently higher than the systolic blood pressure of the measurement subject (e.g., systolic blood pressure+30 mmHg), and it is stored in advance in the memory 51 or it is determined by the CPU 100 estimating the systolic blood pressure using a predetermined calculation equation while the cuff pressure is increased (e.g., see JP 2001-70263A).

Also, as for the pressure decrease rate, a target pressure decrease rate that is to be a target is set while the cuff is being inflated, and the CPU 100 controls the degree of opening of the valve 33 so as to reach the target pressure decrease rate (see JP 2001-70263A).

In the pressure decrease process, the cuff pressure signal (indicated by reference sign Pc) representing the pressure in the cuff 20 is detected by the pressure sensor 31 via the cuff 20. Based on the cuff pressure signal Pc, the CPU 100 calculates the blood pressure values (systolic blood pressure and diastolic blood pressure) by applying a later-described algorithm using an oscillometric method (step ST104). Note that the calculation of the blood pressure values is not limited to the pressure decrease process and may be performed in the pressure increase process.

When the blood pressure values are calculated and determined (YES in step ST105), the CPU 100 performs control for displaying the calculated blood pressure values on the display device 50 (step ST106) and storing the blood pressure values in the memory 51 (step ST107).

Next, when the stopping switch 52C is pressed, the CPU 100 performs control for opening the valve 33 via the valve driving circuit 330 and discharges the air in the fluid bladder 22 of the cuff 20 (step ST108).

When the power supply switch 52A is pressed thereafter, blood pressure measurement is ended.

With the electronic blood pressure monitor 1, the plunger 6 and the valve body 61 can be replaced easily in the valve 33. Accordingly, various different flow rate properties can be easily realized without changing the entire valve 33. Also, maintenance can be easily performed on the interior of the valve 33.

The above-described embodiment is merely an example and may be modified in various ways without departing from the scope of the claimed invention.

REFERENCE NUMERALS LIST

2 Solenoid valve
3 Yoke
4 Core
6 Plunger
7 Coil unit
8 Bobbin
9 Solenoid coil
84, 85 Lock portion
90 Yoke lid
90m Through hole

The invention claimed is:

1. A solenoid valve capable of variably controlling a flow amount of a fluid, comprising:
  a casing comprising a through hole formed therethrough;
  a bobbin accommodated in the casing and including a lock portion extending from an outer surface of the casing;

a solenoid coil wound around the bobbin;
a rod-shaped plunger slidably inserted in the bobbin;
a core that is provided with a flow port through which the fluid flows and is disposed on a side of the casing opposing one end of the rod-shaped plunger;
a valve body that is provided on the one end of the rod-shaped plunger and is disposed so as to oppose the flow port; and
a biasing portion that biases the rod-shaped plunger in a direction of moving away from the core,
wherein, in a non-operating period, during which the solenoid coil is in a non-energized state, the valve body provided on the one end of the rod-shaped plunger moves away from the flow port and another end opposite to the one end of the rod-shaped plunger protrudes outward from the casing through the through hole, abuts against the lock portion disposed outside of the casing, and is thereby locked,
wherein in a working period during which the solenoid coil is in an energized state, the flow amount of the fluid flowing through the flow port is adjusted due to the rod-shaped plunger and the valve body being moved inside the bobbin against a biasing force applied by the biasing portion, due to a magnetic force generated by the solenoid coil,
wherein the lock portion can deform elastically due to an external force such that separation of the rod-shaped plunger and the valve body from the casing is allowed,
wherein the casing has a U-shaped yoke and a plate-shaped yoke lid that closes an open end of the U-shaped yoke, and the through hole is formed in the plate-shaped yoke lid,
wherein the bobbin has a main body portion accommodated in the casing, a first extended portion and a second extended portion formed integrally with the main body portion, and
wherein the first extended portion and the second extended portion come into contact with a pair of opposing sides of the plate-shaped yoke lid and extend outward of the casing through the through hole parallel to a movement path of the rod-shaped plunger, and constitute the lock portion.

2. The solenoid valve according to claim 1,
wherein each of the first and second extended portions includes:
  an arm portion that extends outward of the casing through the through hole along the movement path of the rod-shaped plunger, a leading end side of the arm portion being able to bend in a direction of moving away from the movement path of the rod-shaped plunger due to the external force; and
  a hook portion that extends substantially orthogonally toward the movement path of the rod-shaped plunger from the leading end of the arm portion, and wherein the hook portion locks the other end of the rod-shaped plunger during the non-operating period.

3. The solenoid valve according to claim 2,
wherein the through hole includes a main region having a shape that substantially corresponds with a cross-section of the rod-shaped plunger, and an extended region that is continuous with the main region and is extended in order to allow the arm portion to pass therethrough, and
wherein a gap is provided between the arm portion and a face opposing the arm portion of the extended region, with respect to at least the direction in which the arm portion moves away from the movement path of the rod-shaped plunger.

4. The solenoid valve according to claim 2, wherein the hook portion includes a tapered surface provided on a side opposite to a side that abuts against the rod-shaped plunger.

5. The solenoid valve according to claim 2, wherein the lock portion further comprising a plurality of sets of first and second extended portions formed integrally with the main body portion that are each composed of the arm portion and the hook portion.

6. The solenoid valve according to claim 1,
wherein a direction in which the pair of sides of the plate-shaped yoke lid oppose each other substantially matches a direction in which the lock portion receives the external force about the movement path of the rod-shaped plunger.

7. An electronic blood pressure monitor configured to measure blood pressure at a measurement site, the blood pressure monitor comprising: a
  cuff adapted to be attached at the measurement site;
  a pump for supplying air to the cuff;
  a solenoid valve; and
  a control unit configured to increase pressure in the cuff by supplying air to the cuff using the pump and reduce the pressure in the cuff by ejecting air through the solenoid valve from the cuff, and thereby control the pressure in the cuff;
wherein the solenoid valve comprises:
  a casing comprising a through hole formed therethrough;
  a bobbin accommodated in the casing and including a lock portion extending from an outer surface of the casing;
  a solenoid coil wound around the bobbin;
  a rod-shaped plunger slidably inserted in the bobbin;
  a core that is provided with a flow port through which a fluid flows and is disposed on a side of the casing opposing one end of the rod-shaped plunger;
  a valve body that is provided on the one end of the rod-shaped plunger and is disposed so as to oppose the flow port; and
  a biasing portion that biases the rod-shaped plunger in a direction of moving away from the core,
wherein, in a non-operating period, during which the solenoid coil is in a non-energized state, the valve body provided on the one end of the rod-shaped plunger moves away from the flow port and another end opposite to the one end of the rod-shaped plunger protrudes outward from the casing through the through hole, abuts against the lock portion disposed outside of the casing, and is thereby locked,
wherein in a working period during which the solenoid coil is in an energized state, the flow amount of the fluid flowing through the flow port is adjusted due to the rod-shaped plunger and the valve body being moved inside the bobbin against a biasing force applied by the biasing portion, due to a magnetic force generated by the solenoid coil,
wherein the lock portion can deform elastically due to an external force such that separation of the rod-shaped plunger and the valve body from the casing is allowed,
wherein the casing has a U-shaped yoke and a plate-shaped yoke lid that closes an open end of the U-shaped yoke, and the through hole is formed in the plate-shaped yoke lid, wherein the bobbin has a main body portion accommodated in the casing, a first extended portion and a second extended portion formed integrally with the main body portion, and wherein the first extended portion and the second extended portion come into contact with a pair of opposing sides of the plate-shaped yoke lid and extend outward of the casing through the through hole parallel to a movement path of the rod-shaped plunger, and constitute the lock portion.

* * * * *